US00PP11657P

United States Patent [19]

van Rijn

[11] Patent Number: Plant 11,657

[45] Date of Patent: Nov. 28, 2000

[54] ANTHURIUM PLANT NAMED 'PINK PARADISE'

[75] Inventor: Leonardus van Rijn, Schipluiden, Netherlands

[73] Assignee: Rijnplant, Schipluiden, Netherlands

[21] Appl. No.: 09/291,095

[22] Filed: Apr. 14, 1999

[51] Int. Cl.[7] ..... A01H 5/00

[52] U.S. Cl. ..... Plt./365

[58] Field of Search ..... Plt./367, 365

*Primary Examiner*—Howard J. Locker
*Assistant Examiner*—Anne Marie Grünberg
*Attorney, Agent, or Firm*—C. A. Whealy

[57] ABSTRACT

A distinct cultivar of Anthurium plant named 'Pink Paradise', characterized by its upright plant habit; freely clumping growth habit; durable dark green leaves that are ovate to lanceolate in shape; numerous inflorescences that are positioned upright and beyond the foliage on strong and erect scapes; durable, glossy pink spathes with light green lobes; year-round continuous flowering; good flowering under low light conditions; and good post-production longevity.

1 Drawing Sheet

BACKGROUND OF THE INVENTION

The present invention relates to a new and distinct cultivar of Anthurium plant, botanically known as *Anthurium andreanum*, and hereinafter referred to by the cultivar name 'Pink Paradise'.

The new Anthurium is a product of a planned breeding program conducted by the Inventor in Schipluiden, The Netherlands. The objective of the program is to create and develop new Anthurium cultivars that have a freely clumping growth habit, strong and vigorous plant growth, attractive spathe color, numerous inflorescences and leaves, and good post-production longevity.

The new Anthurium originated from a self-pollination by the Inventor in August, 1994 of the Inventor's proprietary *Anthurium andreanum* selection code number 92-7. The cultivar 'Pink Paradise' was discovered and selected by the Inventor as a plant within the progeny of the stated cross in a controlled environment in Schipluiden, The Netherlands in September, 1996.

Asexual propagation of the new cultivar by tissue culture has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar 'Pink Paradise'. These characteristics in combination distinguish 'Pink Paradise' as a new and distinct cultivar:

1. Upright plant habit.
2. Freely clumping growth habit.
3. Durable dark green leaves that are ovate to lanceolate in shape.
4. Numerous inflorescences that are positioned upright and beyond the foliage on strong and erect scapes.
5. Durable, glossy pink spathes with light green lobes.
6. Year-round continuous flowering.

7. Good flowering under low light conditions.
8. Good post-production longevity.

The new Anthurium can be compared to the parent, the Inventor's proprietary selection code number 92-7. In side-by-side comparisons conducted by the inventor in Schipluiden, The Netherlands, plants of the new Anthurium differ from plants of selection code number 92-7 in the following characteristics:

1. Plants of the new Anthurium have smaller and more durable leaves than plants of the selection code number 92-7.
2. Plants of the new Anthurium have dark pink-colored spathes whereas plants of the selection code number 92-7 have red-colored spathes.

The new Anthurium can be compared to the Anthurium cultivar 'Eveline', disclosed in U.S. Plant Pat. No. 10,970. In side-by-side comparisons conducted by the Inventor in Schipluiden, The Netherlands, plants of the new Anthurium differ from plants of the cultivar 'Eveline' in the following characteristics:

1. Plants of the new Anthurium grow faster than plants of the cultivar 'Eveline'.
2. Plants of the new Anthurium have more durable and glossier leaves than plants of the cultivar 'Eveline'.
3. Leaf apices of plants of the new Anthurium are more acute than leaf apices of plants of the cultivar 'Eveline'.

BRIEF DESCRIPTION OF THE PHOTOGRAPH

The accompanying colored photograph illustrates the overall appearance of the new Anthurium, showing the colors as true as it is reasonably possible to obtain in colored reproductions of this type. The photograph comprises a top perspective view of a typical potted plant of the cultivar 'Pink Paradise'. Leaf, spathe and spadix colors in the photograph may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe 2.5-years old plants grown in 17-cm containers in Schipluiden, The Netherlands, in a glass greenhouse with an average day temperature of 25° C. and an average night temperature of 19° C.

Botanical classification: *Anthurium andreanum* cultivar 'Pink Paradise'.

Parentage: Self-pollination of Inventor's proprietary *Anthurium andreanum* selection code number 92-7.

Propagation:

*Method.*—Typically by tissue culture.

*Time to initiate roots.*—About 70 or 84 days at 24° C. or 21° C., respectively.

*Rooting habit.*—Numerous and very strong fleshy roots.

Plant description:

*Plant shape.*—Upright, inverted triangle, symmetrical.

*Growth habit.*—Freely clumping, bushy and dense, about four to six shoots per plant. Appropriate for 17 to 40-cm containers.

*Plant height.*—About 40 to 55 cm from soil level to apex of spathes.

*Plant width.*—About 70 to 80 cm.

*Plant vigor.*—High.

*Growth rate.*—Rapid.

*Crop time.*—About 8 and 16 months are usually required from planting of young plants to finished plants in 17 and 40-cm containers, respectively.

*Foliage description.*—Quantity: Usually about two to four per shoot; about 8 to 24 leaves per plant. Length: About 17 to 30 cm. Width: About 13 to 18 cm. Shape: Ovate to lanceolate. Apex: Apiculate to cuspidate. Base: Strongly auriculate; lobes not overlapping. Margin: Entire. Texture: Smooth, glabrous, leathery. Color: Young leaves, upper surface: 144A to 146A. Young leaves, lower surface: 146D with gray. Mature leaves, upper surface: Darker than 137A. Mature leaves, lower surface: Close to 146B to 144A. Petiole: Length: About 28 to 40 cm. Color: Close to 144A. Geniculum length: About 2 to 3 cm. Geniculum diameter: About 3 to 5 mm. Geniculum color: 144A to 144B.

Inflorescence description:

*Inflorescence arrangement.*—Spathes with spadices held beyond the foliage. Flowering structures arise from leaf axils. Freely flowering; continuous flowering year-round; numerous spathes/spadices per plant.

*Inflorescence longevity.*—Spathes/spadices last about six weeks under winter conditions and about three months under summer conditions; persistent.

*Flowers.*—Quantity per spadix: Numerous, about 150 to 200. Shape: Rounded. Diameter: About 1 mm, maximum.

*Spathe.*—Length: About 7 to 9 cm. Width: About 11 to 13 cm. Shape: Very broadly cordate. Apex: Apiculate to cuspidate. Base: Straight. Margin: Entire. Texture: Leathery, glabrous, very slight blistering, glossy. Color: When opening: 52A to 52C. Front surface: Center, 52A to 50A; lobes, light green, close to 143C to 140B. Back surface: 55C to 54C; lobes, 143B. After senescence: Center, 52A to 50A, dull; lobes, 143A to 143B.

*Spadix.*—Length: About 5 to 6 cm. Diameter: Midsection, about 6 to 7 mm; apex, about 4 mm. Shape: Columnar. Cross section: Rounded. Longitudinal axis: Straight. Color: Base and mid-section: 48C to 48D. Apex: 30A. After senescence: Close to 151A.

*Scape.*—Length: About 35 to 45 cm. Aspect: Strong and erect, slight bending. Color: 144A; anthocyanin towards apex, purplish, 59A.

*Reproductive organs.*—Androecium: Pollen color: Creamy white, 158D. Gynoecium: Stigma shape: Ovoid. Ovary: Protogyneous.

Disease resistance: Plants of the new Anthurium have exhibited good resistance to root diseases common to Anthurium.

Seed development: Seed development on plants of the new Anthurium has not been observed.

It is claimed:

1. A new and distinct cultivar of Anthurium plant named 'Pink Paradise', as illustrated and described.

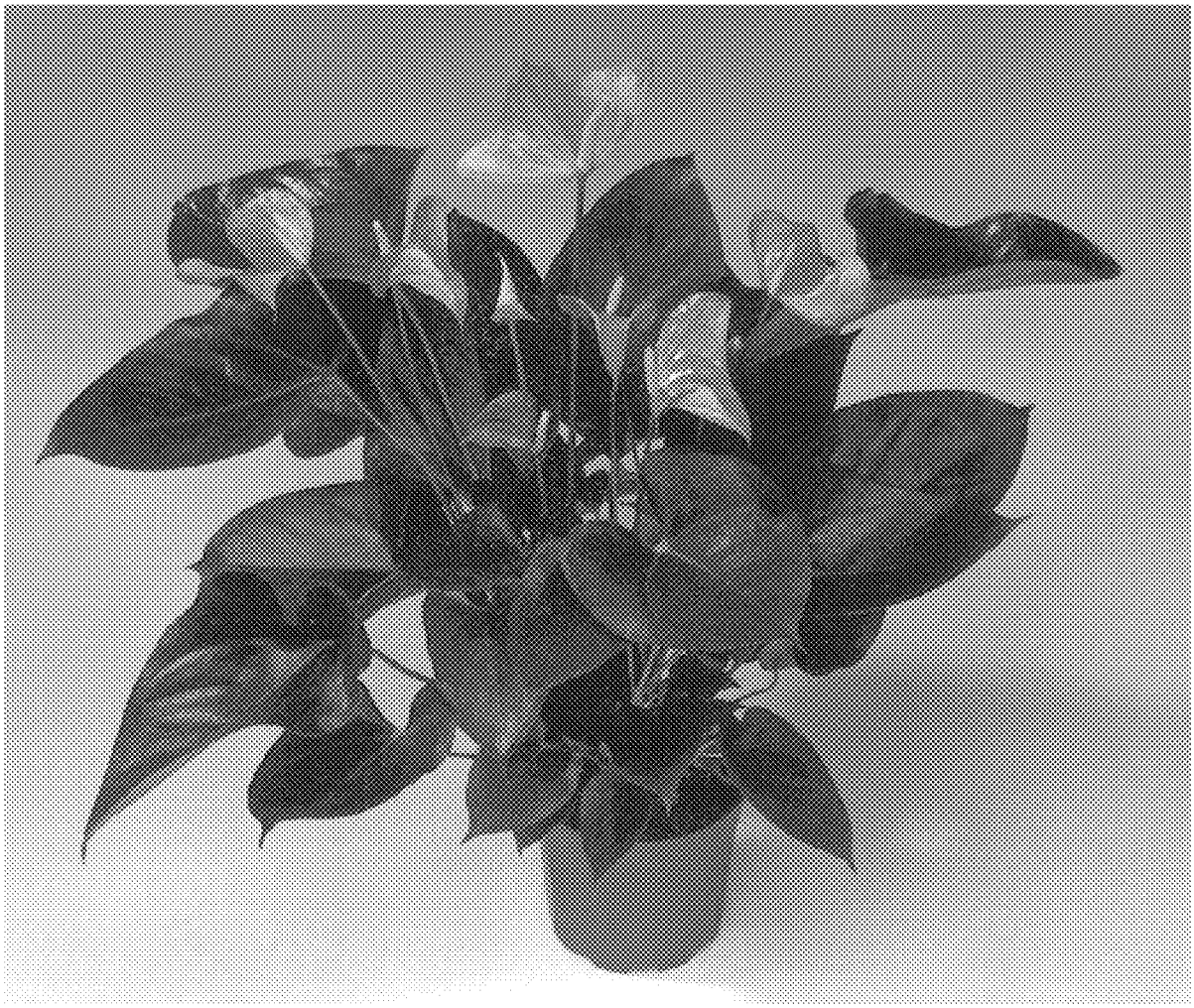

* * * * *